(12) United States Patent
Myung et al.

(10) Patent No.: US 7,820,113 B2
(45) Date of Patent: Oct. 26, 2010

(54) DEVICE FOR SIMULTANEOUSLY COLLECTING FILTERED WATER AND FILTER PAPER

(75) Inventors: Cheol-Soo Myung, 101-1306 Dongman Apt., 943, Dongchoon 2-dong, Yunsoo-ku, Incheon (KR) 406-756; Sin-Jae Yoo, Kyunggi-do (KR)

(73) Assignees: Korea Ocean Research and Development Institute, Kyunggi-do (KR); Cheol-Soo Myung, Inchon (KR)

( * ) Notice: Subject to any disclaimer, the term of this patent is extended or adjusted under 35 U.S.C. 154(b) by 1336 days.

(21) Appl. No.: 10/499,192

(22) PCT Filed: Dec. 18, 2002

(86) PCT No.: PCT/KR02/02388

§ 371 (c)(1),
(2), (4) Date: Apr. 21, 2005

(87) PCT Pub. No.: WO03/052384

PCT Pub. Date: Jun. 26, 2003

(65) Prior Publication Data

US 2005/0226783 A1 Oct. 13, 2005

(30) Foreign Application Priority Data

Dec. 18, 2001 (KR) .................. 10-2001-0080942

(51) Int. Cl.
*B01D 63/00* (2006.01)
*B01D 29/00* (2006.01)
*C02F 1/00* (2006.01)

(52) U.S. Cl. ............... 422/101; 210/323.1; 210/455; 210/650; 210/416.1

(58) Field of Classification Search .......... 422/101; 210/323.1, 455, 650, 416.1
See application file for complete search history.

(56) References Cited

U.S. PATENT DOCUMENTS 4,087,362 A * 5/1978 Hutto, Jr. ............... 210/249

(Continued)

FOREIGN PATENT DOCUMENTS

DE 29 24 130 12/1980

(Continued)

OTHER PUBLICATIONS

International Search Report for PCT/KR02/02388 mailed Apr. 7, 2003.

(Continued)

*Primary Examiner*—Jill Warden
*Assistant Examiner*—Paul S Hyun
(74) *Attorney, Agent, or Firm*—RatnerPrestia

(57) ABSTRACT

The present invention relates to filtering a collected sample for water analysis, and a device where filtered water is collected so that filtered water can be contained in a sample container and where the collecting rate of the sample can be controlled. The collecting device comprises at least one filter funnel part, an upper plate on which the funnel part placed, mounting device comprising a supporting rod wherein one side of the supporting rod is combined with the edge of the upper plate and a waste box fixing the supporting rod, several base container parts wherein the sample container is inserted and a outlet port is formed, and a vacuum pump connected to the vacuum connecting port by a pump tube. Accordingly, the step of transferring filtered water into the sample container can be omitted, and the collection time can be reduced by controlling the collecting rate of the sample.

8 Claims, 5 Drawing Sheets

U.S. PATENT DOCUMENTS

| | | | | |
|---|---|---|---|---|
| 4,235,677 A | * | 11/1980 | Karamian | 202/176 |
| 4,247,399 A | | 1/1981 | Pitesky | |
| 4,783,318 A | | 11/1988 | Lapakko | |
| 4,832,842 A | * | 5/1989 | Limb | 210/249 |
| 4,890,484 A | | 1/1990 | Telfer et al. | |
| 5,141,719 A | * | 8/1992 | Fernwood et al. | 422/101 |
| 5,183,259 A | * | 2/1993 | Lyon | 473/581 |
| 5,380,437 A | | 1/1995 | Bertoncini | |
| 5,753,105 A | | 5/1998 | Johnson | |
| 5,976,824 A | | 11/1999 | Gordon | |
| 6,159,368 A | | 12/2000 | Moring et al. | |
| 6,336,567 B1 | * | 1/2002 | Hyobu | 220/230 |
| 6,338,802 B1 | * | 1/2002 | Bodner et al. | 210/650 |
| 6,436,351 B1 | * | 8/2002 | Gubernator et al. | 422/102 |
| 6,491,873 B2 | * | 12/2002 | Roberts et al. | 422/101 |
| 6,808,931 B1 | * | 10/2004 | Wang et al. | 436/83 |
| 2001/0001643 A1 | * | 5/2001 | Simpson et al. | 422/101 |
| 2003/0223912 A1 | * | 12/2003 | Knecht et al. | 422/100 |
| 2005/0266585 A1 | * | 12/2005 | Bargh | 436/177 |

FOREIGN PATENT DOCUMENTS

| | | |
|---|---|---|
| EP | 0 857 961 A2 | 8/1998 |
| JP | 56-092430 | 7/1981 |
| JP | 09-015120 A | 1/1997 |
| JP | 2000-146948 | 5/2000 |
| KR | 1995-0016817 | 7/1995 |

OTHER PUBLICATIONS

Supplementary European Search Report for EP 02 79 3488 mailed Jul. 17, 2008.

* cited by examiner

DEVICE FOR SIMULTANEOUSLY COLLECTING FILTERED WATER AND FILTER PAPER

This application is a U.S. National Phase Application of PCT International Application No. PCT/KR02/02388, filed Dec. 18, 2002.

TECHNICAL FIELD

The present invention relates to a device for analyzing the quality of liquid, more particularly to a device for collecting simultaneously the filter paper through which the sampled water is filtered (hereinafter referred as "the served filter paper") and the water which is filtered through the filter paper (hereinafter referred as "the filtered water"). Water is generally sampled from the sources such as domestic water, wells, ponds, rivers, lakes, the sea, etc.

BACKGROUND OF THE INVENTION

As well known to those skilled in the art, there have been disclosed several kinds of water sampling devices to sample water from such sources as wells, ponds, rivers, lakes, the sea, etc, at a given depth. As a prior step to analyze a pollution level, bacteria, organisms, compositions, etc. of the water sampled by the water sampling devices or other means, the sampled water is filtered through a porous filter paper. Subsequently, the served filter paper and the filtered water are collected at the same time. As such, there has been proposed a filtering device capable of simultaneously collecting the served filter paper and the filtered water.

As shown in FIG. 1, the conventional filtering device for both pressuring and decompressing comprises a funnel-shaped filtering unit 1 and a flask 10. The sampled water is filtered through the filter paper 4 of the funnel-shaped filtering unit 1 and the filtered water flows into the flask 10.

Said funnel-shaped filtering unit 1 comprises an influx container 2, a seat 6, a feeding pipe 7, and a plug 9 which is holed through. The influx container 2 is cup-shaped without the bottom. A flange 3 is provided around an outer edge of the open bottom of the influx container 2. The sampled water for analyzing is fed into an upper portion of the funnel-shaped filtering unit 1, such that the sampled water flows downward. The seat 6 is holed through. A mesh 5 is placed on the seat 6 to support the filter paper 4, and then the flange 3 of the influx container 2 is seated on the seat 6. A feeding pipe 7 downwardly extends from the seating part 6. The feeding pipe 7 and the seat 6 may be a single body. Alternatively, the feeding pipe 7 and the seat 6 may be assembled when they are used. The plug 9 is holed through along its center and the feeding pipe 7 is fitted into the through hole of the plug 9.

Said flask 10 is provided at its upper portion with a drain port 11 through which air or the filtered water passes. The plug 9 is fitted into the mouth 12 of the flask 10. A tube (not shown) may be connected to the drain port 11 to drain the surplus filtered water from the flask 10. Further, a vacuum pump (not shown) may be connected to the tube.

In such said conventional device, the sampled water fed into the influx container 2 is filtered through the filter paper 4 which is interposed between the flange 3 of the influx container 2 and the seat 6, and almost all of the filtered water which is filtered through the filter paper 4 flows into the flask 10 via the feeding pipe 7 which extends downwardly from the seat 6.

So it is possible to collect the served filter paper 4 and the filtered water from the conventional device simultaneously.

However, in order to transfer the filtered water in the flask 10 to the filtered water container 15, the plug 9 of the funnel-shaped filtering unit 1 must be detached from the flask 10 and then the filtered water in the flask 10 must be poured into the filtered water container 15. So it is inconvenient to use the conventional device and the filtered water may be polluted during the transferring step of the conventional device.

Furthermore, because the conventional device is designed such that the sampled water flows downwards due to the gravity, it takes a considerably long time to filter the sampled water through the filter paper 4. And the filtered water may be not fed into the flask 10 when the filter paper 4 is clogged with the impurities of the sampled water. In order to solve the problems, the vacuum pump is connected to the drain port 11 of the flask 10. When the vacuum pump is operated to generate negative pressure in the flask 10, the sampled water may be filtered through the filter paper 4 more rapidly. However, the filtered water may be fed into the flask 10 above the drain port 11 and then the filtered water may flow into the vacuum pump. Thus, in order to prevent the filtered water from feeding into the flask 10 above the drain port 11, it is necessary to observe whether the filtered water is fed in the filtered water container above the drain port 11 or not and transfer the filtered water in the flask 10 to another container before the filtered water is fed above the drain port 11.

So it is inconvenient and troublesome to use the conventional device.

BRIEF SUMMARY OF THE INVENTION

The present invention has been made keeping in mind the problem mentioned above. According to the present invention, the filtered water is directly fed into the filtered water container, so that the funnel-shaped filtering unit needs not to be detached from the flask to transfer the filtered water in the flask to the filtered water container, that is the transferring step is not needed. So the possibility of the pollution happened during the transferring step can be minimized. In order to reduce the time to filter the sampled water through the filter paper, the vacuum pump is used to generate the negative pressure in the filtered water storage unit in the present invention. The collecting rate is controlled by the vacuum pump and the additional storage space is provided. It is possible to prevent the filtered water from flowing over the filtered water container and it is not necessary to observe whether the filtered water flows over the filtered water container or not. Thus it is possible to perform another work while collecting the served filter paper and the filtered water with the device according the present invention.

To make all the things mentioned above possible, the present invention provides a device simultaneously collecting the served filter paper and the filtered water. The device according to the present invention comprises at least one funnel-shaped filtering unit, a supporting unit, a drain tank, a mounting means, at least one filtered water storage unit of the same number as that of the funnel-shaped filtering units, and a vacuum pump. A funnel-shaped filtering unit comprises an influx container holed through to allow water to pass therethrough, a seat seated on the flange of the influx container in such a way that a filter paper is interposed between the influx container and the seat, and a plug provided with a through hole in which the feeding pipe is fitted. The feeding pipe extends vertically and downwardly from a lower part of the seat. A supporting unit comprises a supporting plate having at least one support through hole, at least one plug support blocks, at least one sealing means provided on a lower surface of the supporting plate, and at least one first attaching means provided on the lower surface of the supporting plate at a position outside the sealing means, wherein the number of the plug support blocks, the sealing means and the first attaching means is the same as that of the support through holes.

A plug support block comprises a large-diameter hollow part and a small-diameter hollow part. The plug is fitted into the large-diameter hollow part and the small-diameter hollow part is fitted into the support through hole to be sealed. A drain tank defines a space therein and comprises the tube connecting through holes of the same number as that of the support through holes, a vacuum pump connecting through hole provided at a predetermined position of the top surface of the drain tank, a discharging through hole formed at a predetermined position of a lower part of the drain tank and a shut-off cock placed at the discharging through hole. The tube connecting through holes are placed at the top surface of the drain tank at regular intervals. A mounting means comprises the supporting rods to support the supporting unit, so that the supporting unit is spaced apart from the drain tank at a predetermined distance. A filtered water storage unit comprises the main bodies of the same number as that of the support through holes and the drain tubes. The main body is opened at its top, defines a space therein to hold the filtered water container for collecting the filtered water, has a flange extending around its upper part and is provided with a second attaching means to be attached to the first attaching means of the supporting unit. One end of the drain tube is connected to the drain through hole formed at a center of a bottom of the main body and the other end is connected to the tube connecting through hole of the drain tank. A vacuum pump is connected to the vacuum pump connecting through hole via a pump tube.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
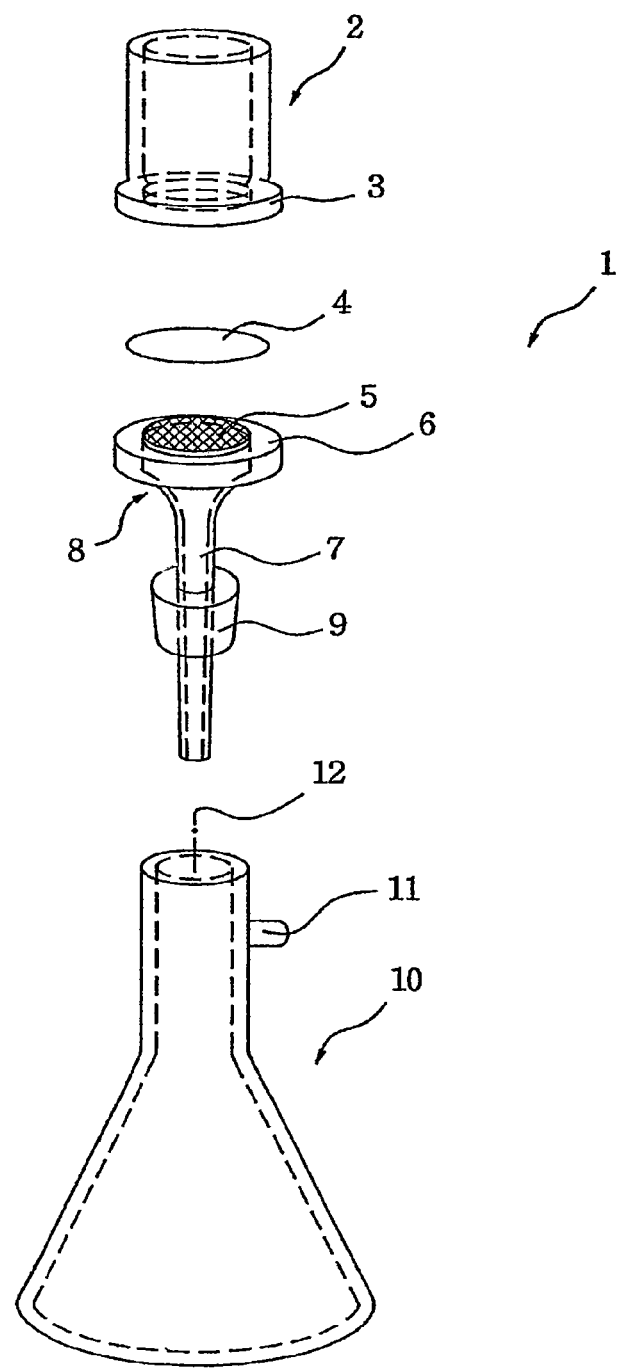
FIG. 1 is a perspective view showing the conventional device for collecting the filtered water and the served filter paper.
Figure 2:
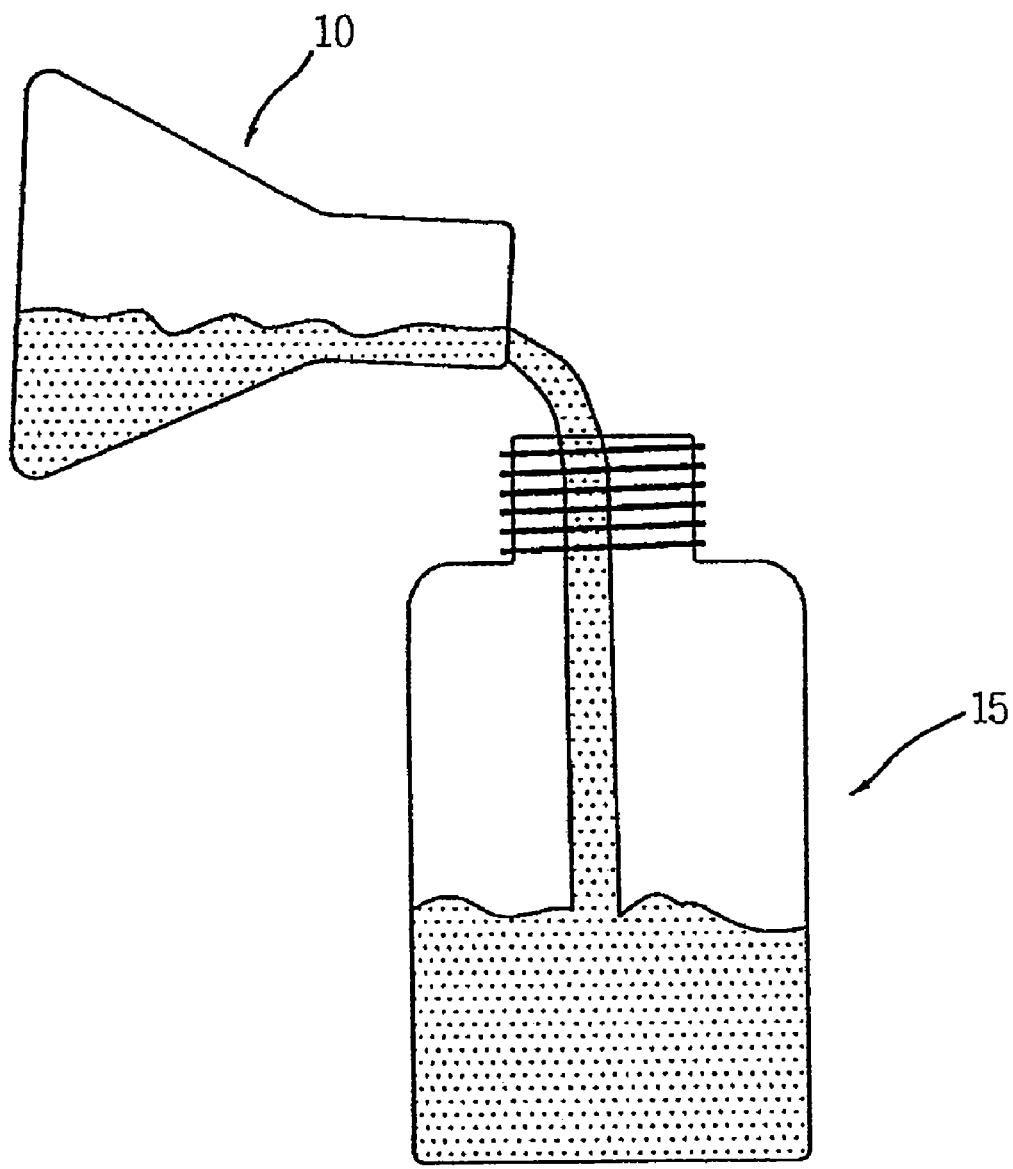
FIG. 2 is a front view showing the step which the filtered water in the flask of the conventional device is transferred to the filtered water container.

Reference should now be made to the drawings, in which the same reference numerals are used throughout the different drawings to designate the same components.

Figure 3:
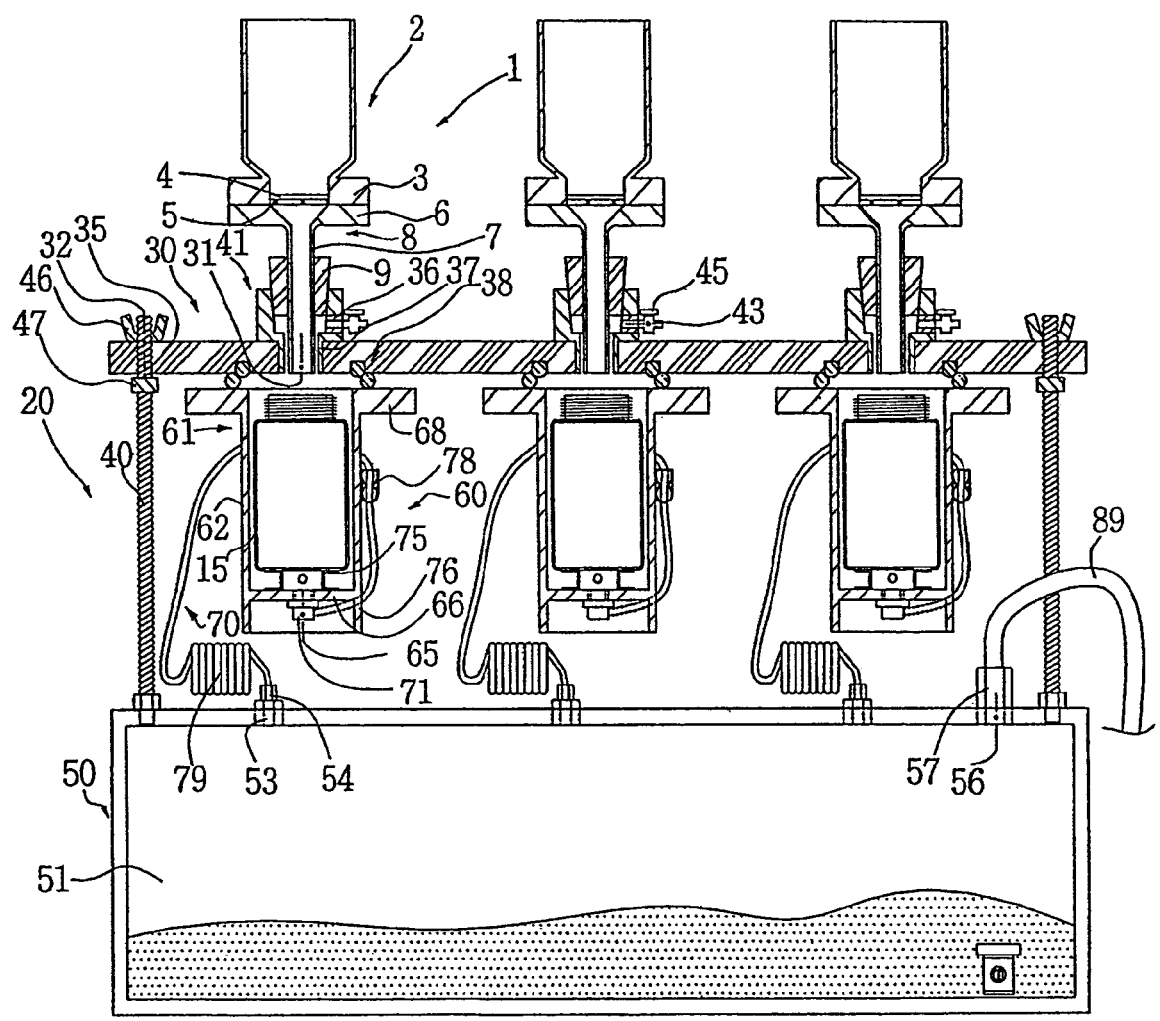
FIG. 3 is a front sectional view showing the device for simultaneously collecting the filtered water and the served filter paper according to an embodiment of the present invention.

FIG. 3 is a front sectional view showing a device for simultaneously collecting the filtered water and the served filter paper according to an embodiment of the present invention.

Figure 4:
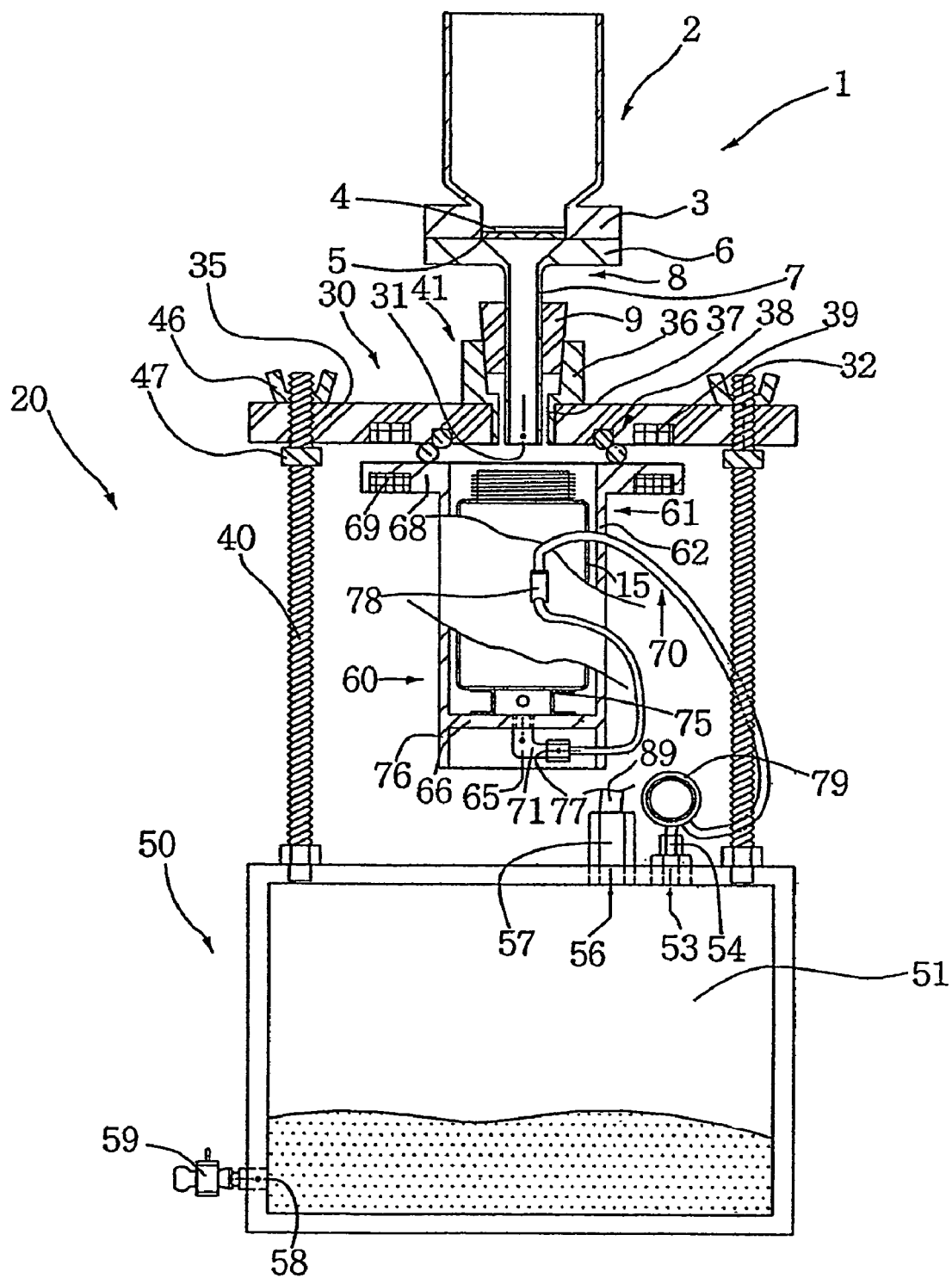
FIG. 4 is a side sectional view showing the device for simultaneously collecting the filtered water and the served filter paper according to an embodiment of the present invention.
Figure 5:
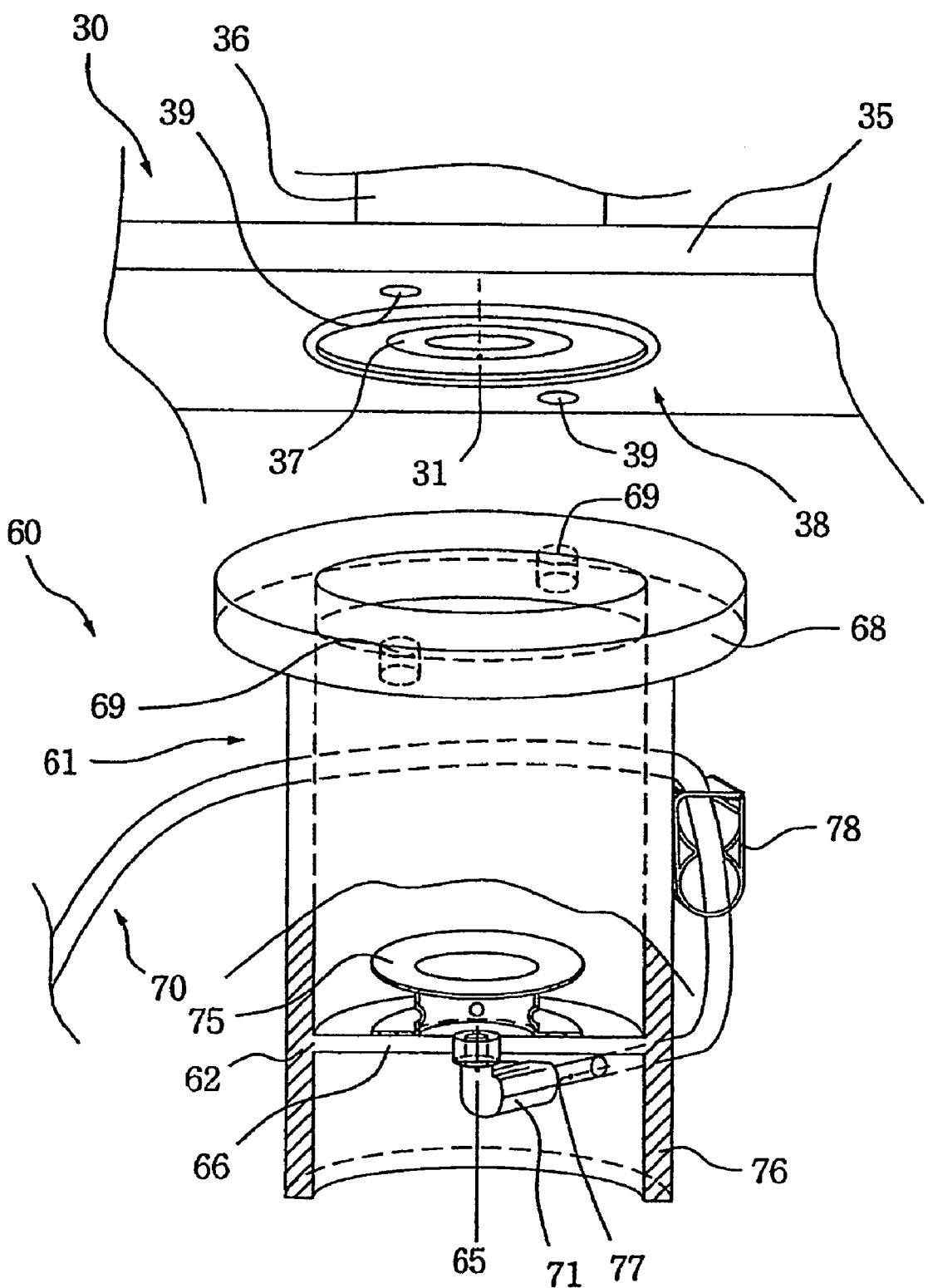
FIG. 5 is a perspective view showing the device for simultaneously collecting the filtered water and the served filter paper according to an embodiment of the present invention, which a filtered water storage unit is detached from a supporting unit.

FIG. 4 is a side sectional view showing the device for simultaneously collecting the filtered water and the served filter paper according to an embodiment of the present invention. FIG. 5 is a perspective view showing the device for simultaneously collecting the filtered water and the served filter paper according to an embodiment of the present invention, which the filtered water storage unit is detached from a supporting unit.

As shown in FIGS. 3 and 4, the device for simultaneously collecting the filtered water and the served filter paper according to the present invention comprises the funnel-shaped filtering unit 1, the mounting means 20, the filtered water storage unit 60, and the vacuum pump (not shown).

The funnel-shaped filtering unit 1 comprises an influx container 2, a feeding unit 8, and a plug 9. In this case, the influx container 2 tapers off from its upper end, so the diameter of its upper part is larger than that of the lower part. A flange 3 is integrally provided at the lower end of the influx container 2, so that the influx container 2 is seated on a seat 6 by the flange 3. The sampled water collected for analyzing is fed into an upper portion of the funnel-shaped filtering unit 1. The sampled water is discharged downwards through the filter paper 4. The feeding unit 8 is holed through vertically to form a vertical passage. A filtering mesh 5 is seated on the upper end of the seat 6 to support the filter paper 4. The seat 6 is removably seated on the flange 3 of the influx container 2. A feeding pipe 7 extends vertically and downwardly from the seat 6. In this case, the feeding pipe 7 and the seat 6 may be a single body or may be assembled when they are used. Along its center, the plug 9 is provided with a through hole into which the feeding pipe 7 is fitted.

The magnets having opposite polarities may be provided in the flange 3 and the seat 6, respectively. It is desirable that the inner diameter of the feeding pipe 7 is smaller than that of the lower part of the influx container 2. Further, in order to allow the whole filtered water passing through the feeding pipe 7 to flow into the filtered water container 15, the inner diameter of the feeding pipe 7 must be smaller than that of the mouth of a filtered water container 15. And it is preferable that the plug 9 tapers off downwards, so that the diameter of its lower part of the plug is smaller than that of its upper part.

The mounting means 20 comprises a supporting unit 30, supporting rods 40 and a drain tank 50.

The supporting unit 30 comprises a supporting plate 35, a plug support block 41, a sealing means 38 and a first attaching means 39. The shape of the supporting plate 35 is rectangular. At least one support through hole 31 is formed in the supporting plate 35 at regular intervals, and the guide through holes 32 are formed at four corners of the supporting plate 35. The plug support block 41 comprises the large-diameter hollow part 36 and the small-diameter hollow part 37. The number of the plug support blocks 41 is the same as that of the support through holes 31. The plug 9 of the funnel-shaped filtering unit 1 is fitted into the large-diameter hollow part 36 to be sealed. The small-diameter hollow part 37 is fitted into the support through hole 31 to be sealed. Further, the sealing means 38 of the same number as that of the support through holes 31 are provided on a lower surface of the supporting plate 35 at a position around the support through hole 31. The first attaching means 39 is provided on the lower surface of the supporting plate 35 at a position outside the sealing means 38 and the number of the first attaching means 39 is the same as that of the support through holes 31.

The inner diameter of the small-diameter hollow part 37 of the plug support block 41 is larger than the outer diameter of the feeding pipe 7, so that the feeding pipe 7 of the funnel-shaped filtering unit 1 extends into the small-diameter hollow part 37. In this case, the plug support block 41 having the large-diameter hollow part 36 and the small-diameter hollow part 37 or the plug support block 41 having only the large-diameter hollow part 36 may be integrated with the supporting plate 35.

A ventilating through hole 43 is formed at the large-diameter hollow part 36 of the plug support block 41. A vacuum release valve 45 is provided at the ventilating through hole 43, and is opened or closed to release or maintain vacuum.

The sealing means 38 may comprise a rubber ring. A circular groove having a rectangular cross-section is formed at the lower surface of the supporting plate 35 so that the rubber ring is inserted into the groove. Further, the sealing means 38 may comprise two pieces of neighboring rubber rings, that is the first rubber ring and the second rubber ring. The first rubber ring is inserted into the circular groove whose cross-section is rectangular and is formed at the lower surface of the supporting plate 35. The second rubber ring is provided along an outer circumference of the first rubber ring in such a way as to be attached to the first rubber ring at a plurality of contacts provided at several positions, and the diameter of the second rubber ring is larger than that of the first rubber ring.

One end of the supporting rod 40 is fitted into the guide through holes 32 which are formed at the supporting unit 30, and the other end is mounted on the edge of the top surface of the drain tank 50. In this case, the supporting rod 40 is threaded externally to engage with the guide through hole 32. The supporting plate 35 of the supporting unit 30 is movable upward or downward relative to the drain tank 50 along the supporting rod 40, and is fastened to a desired position of the supporting rod 40 using a wing nut 46 and a support nut 47 at its upper and lower surfaces.

The drain tank 50 is box-shaped, and defines a space 51 therein to store the filtered water flowing over the filtered water container 15. The tube connecting through holes 53 of the same number as that of the support through holes 31 are formed at the top surface of the drain tank 50 at regular intervals. A first connecting member 54 is assembled to the tube connecting through hole 53. A vacuum pump connecting through hole 56 is provided at a predetermined position of the top surface of the drain tank 50, and a pump connecting member 57 is assembled to the vacuum pump connecting through hole 56. Further, a discharging through hole 58 is formed at a predetermined position of a lower part of the drain tank 50. A shut-off cock 59 is provided at the discharging through hole 58.

As shown in FIG. 5 in detail, the number of the filtered water storage units 60 is the same as that of said support through holes 31. A filtered water storage unit 60 comprises a main body 61, a second connecting member 71 and a drain tube 70. A main body 61 comprises a cylindrical part 62, a flange 68, and a bottom plate 66. The cylindrical part 62 defines a space which is opened at its top so as to hold the filtered water container 15 for containing the filtered water flowing out of the feeding pipe 7 of the funnel-shaped filtering unit 1. The flange 68 outwardly extends around an upper portion of the cylindrical part 62, and is provided with a second attaching means 69 to be removably attached to the first attaching means 39 of the supporting unit 30. The bottom plate 66 is provided in the cylindrical part 62 as shown in FIG. 3. A drain through hole 65 is formed at the center of the bottom plate 66 to drain the filtered water flowing over the filtered water container 15.

The second connecting member 71 is placed at the drain through hole 65 of the main body 61. The filtered water flowing over the filtered water container 15 flows in the drain tank 50 via the drain tube 70 connected to an outlet of the second connecting member 71.

The first attaching means 39 of the supporting unit 30 and the second attaching means 69 of the filtered water storage unit 60 comprise magnets whose polarities are opposite each other, so that the filtered water storage unit 60 is removably attached to the supporting unit 30. According to the embodiment of the present invention, the first and second attaching means 39, 69 comprise two magnets respectively. But the first and second attaching means 39, 69 may comprise three or more magnets respectively. When the first attaching means 39 is attached to the second attaching means 69, the sealing means 38 of the supporting unit 30 contacts closely enough to be sealed with the flange 68 of the filtered water storage unit 60. Although not shown in the drawings, the first and second attaching means 39, 69 may be externally and internally threaded, respectively, so as to engage with each other.

A drain member 75 is provided at the bottom plate 66 of the main body 61, and is provided with a bottom hole at its bottom and with a plurality of side holes at its sidewall. Upper and lower flanges are provided at the upper and lower edges of the drain member 75. Such a drain member 75 allows the surplus filtered water to be smoothly drained through the drain through hole 65. In this case, the various shapes of drain member 75 may be manufactured, but the drain member 75 is necessarily provided with the bottom hole and the side holes. A plurality of grooves may be arranged around the drain through hole 65 on an upper surface of the bottom plate 66 at regular angular intervals in radial directions. Such grooves extend from the drain through hole 65 to the inside of the cylindrical part 62, so that the filtered water flowing over the filtered water container 15 is guided to the drain through hole 65 and smoothly drained.

A hollow extension part 76 downwardly extends from a lower edge of the main body 61. A tube hole 77 is formed at a predetermined position of a sidewall of the hollow extension part 76, so that the drain tube 70 which is connected to the second connecting member 71 passes through the tube hole 77. Thus, when the filtered water storage unit 60 is put on the ground surface or the drain tank 50, it uprightly stands on the ground surface or the drain tank 50 without interfering with the drain tube 70.

A pressure control device 78 is provided at a position of a sidewall of the main body 61 to press the outer surface of the drain tube 70, thus cutting off the negative pressure generated by the vacuum pump, and thereby preventing the negative pressure from being concentrated in the filtered water storage unit 60 when the filtered water storage unit 60 is detached from the supporting unit 30. Thus, although one of several filtered water storage units 60 is detached from the supporting unit 30, the negative pressure in other filtered water storage units 60 is maintained and the collecting can be continued normally.

The drain tube 70 connected to the drain through hole 65 of the filtered water storage unit 60 is long enough to allow the filtered water storage unit 60 to be moved away from the supporting unit 30 when the filtered water storage unit 60 is detached from the supporting unit 30. The drain tube 70 adjacent to the first connecting member 54 is coiled to be neatly arranged, and this prevents said drain tube 70 from drooping and being entangled when said filtered water storage unit 60 is moved to the other place.

The vacuum pump is provided with a pump tube 89. And the pump tube 89 is connected to the pump connecting unit 57 of the drain tank 50. It is possible to control the collecting rate of the filtered water by controlling the pressure generated by the pump.

In the device of the present invention, it is preferable that the components made of rubber or plastics are transparent so that the flow of water may be easily observed.

The method how to operate the device according to the present invention will be described as follows, in detail. At least one funnel-shaped filtering unit 1 and the supporting unit 30 are assembled together by inserting the plug 9 into the plug support block 41.

First, the filter paper 4 is disposed between the influx container 2 and the seat 6 of the funnel-shaped filtering unit 1. Next, the filtered water storage unit 60, which is attached to the supporting unit 30 using the first attaching means 39 of the supporting unit 30 and the second attaching means 69 of the filtered water storage unit 60, is detached from the supporting unit 30. Thereafter, the filtered water container 15 is put into the filtered water storage unit 60. The filtered water storage unit 60 with the filtered water container 15 is attached to the supporting unit 30 again, and is sealed by the sealing means 38.

When the vacuum pump is operated after closing the shut-off cock 59 of the drain tank 50 and the vacuum release valve 45 of the plug support block 41, the negative pressure is generated in the drain tank 50 via the pump tube 89 and the pump connecting member 57. At this time, the negative pressure is transferred to at least one filtered water storage unit 60 for collecting filtered water via the drain tube 70. One end of the drain tube 70 is connected to the first connecting member 54 of the drain tank 50 and the other end is connected to the second connecting member 71 of the filtered water storage unit 60. Because of the difference in pressure between in the storage unit 60 and in the influx container 2, the sampled water in the influx container 2 of the funnel-shaped filtering unit 1 thus forcibly flows downward and is filtered through the filter paper 4. Almost all of the filtered water is fed into the filtered water container 15. The filtered water may flows over the filtered water container 15. But there is nothing to worry about the water flowing into the vacuum pump because the filtered water flown over the filtered water container 15 flows into the drain tank 50 through the drain tube 70 which is connected to the filtered water storage unit 60. When the amount of the filtered water contained in the drain tank 50 exceeds a predetermined level, the shut-off cock 59 of the drain tank 50 is opened to drain.

According to the present invention, the served filter paper 4 and the filtered water may be simultaneously collected using a plurality of the funnel-shaped filtering units 1 and the filtered water containers 15. In this case, when it is required to detach one of the filtered water storage units 60 from the supporting unit 30, the filtered water storage unit 60 may not be easily detached from the supporting unit 30 due to the negative pressure produced in the filtered water storage unit 60. Thus, it is necessary to release the negative pressure from the storage unit 60. The negative pressure of the filtered water storage unit 60 is released by opening the vacuum release valve 45 of the supporting unit 30, which is placed above the filtered water storage unit 60. Further, the pressure cut-off device 78 which is provided at the sidewall of the main body 61 cuts off the filtered water storage unit 60 from the negative pressure by pressing the outer surface of the drain tube 70. Thus, a selected storage unit 60 is easily released from the supporting unit 30 without interrupting the filtering process of the other storage units 60. As such, the device according to the present invention allows the filtered water to be conveniently collected in the several filtered water containers 15 while allowing a number of filter papers 4 to be collected.

When the vacuum pump is not used, it is impossible to control air pressure in the storage units. However, in this case the device of the present invention allows the filtered water and a plurality of filter papers 4 to be simultaneously collected too.

In the present invention, the sampled liquid is not limited to water, and includes other liquids in addition to water. Thus, the device of the present invention is used for simultaneously collecting the filter paper 4 through which the liquid is filtered and the filtered liquid through the filter paper 4.

INDUSTRIAL APPLICABILITY

According to the present invention, because the filtered water directly flows into the filtered water container, the transferring step from the flask to the filtered water container is not needed differently from the conventional device. So it is convenient to use the device according to the present invention while saving time and expense, and minimizing the pollution of the filtered water.

Further, the device according to the present invention is designed to control the filtering rate by using the vacuum pump. Thus it is possible to reduce the time required to discharge the filtered water by controlling the pressure in the filtered water storage unit. Because the filtered water flowing over the filtered water container is drained to the drain tank, it is not needed to observe whether the filtered water flows over the filtered water container or not. Thus, it is possible to perform another work while carrying out the collecting process with the device according the present invention.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A device for simultaneously collecting served filter paper and filtered water through the filter paper for analyzing, comprising:
    plurality of funnel-shaped filtering units, comprising:
        an influx container opened at its top and bottom to allow sampled water to pass through,
        a seat adapted to be removable on a lower end of the influx container in such a way that said filter paper is interposed between the influx container and the seat, with a feeding pipe vertically and downwardly extending from a lower portion of the seat, and
        a plug provided with a through hole in which said feeding pipe is fitted,
    a supporting unit, comprising:
        at least one supporting plate provided with a plurality of support through holes,
        plurality of plug support blocks of the same number as that of said support through holes, which comprises a large-diameter hollow part at an upper portion thereof and a small-diameter hollow part at a lower portion thereof, wherein said large-diameter hollow part closely receives the plug of the funnel-shaped filtering unit, and said small-diameter hollow part is inserted into said support through hole to be sealed,
        a vacuum release valve provided at a position of an outer surface of said plug support block so as to release an internal vacuum state of the plug support block,
        at least one sealing means provided on a lower surface of the supporting plate at a position around said support through holes, and at least one first attaching means provided on the lower surface of the supporting plate at a position outside said sealing means;

a drain tank defining a space therein and comprising:
  first through holes of the same number as that of said support through holes, which is provided at a top surface of the drain tank,
  a second through hole provided at a predetermined position of the top surface of the drain tank,
  a discharging through hole formed at a predetermined position of the lower side of the drain tank, and
  a shut-off cock placed at said discharging through hole;

a mounting means provided with supporting rods to support said supporting unit over said drain tank in such a way that said supporting unit is spaced apart from said drain tank by a predetermined distance;

at least one filtered water storage unit, comprising:
  at least one main body of the same number as that of the support through holes, which is opened at its top and defines a space therein to hold a filtered water container for collecting filtered water, wherein said main body comprises a flange extending around an upper portion of the main body, and provided with a second attaching means to be attached to the first attaching means of said supporting unit and a drain through hole formed at a center of a bottom of the main body, and
  a drain tube whose one end is connected to the drain through hole of the filtered water storage unit and the other end is connected to the tube connecting through hole of the drain tank; and
  a vacuum pump connected the second through hole via a pump tube.

2. The device according to claim 1, wherein a plurality of guide holes are formed at predetermined positions of the supporting unit, and said supporting rod is externally threaded to engage with one of said guide holes, wherein said supporting unit is movable upward or downward relative to said drain tank along said supporting rods, and is fastened, at upper and lower surfaces of the supporting plate thereof, to a predetermined position of the supporting rod using fastening means.

3. The device according to claim 1, wherein said sealing means comprises a rubber ring.

4. The device according to claim 1, which said sealing means comprises neighboring first and second rubber rings, wherein said first rubber ring is fitted into a ring-shaped groove which is formed at the lower surface of the supporting unit, said second rubber ring is provided along an outer circumference of the first rubber ring in such a way as to be attached to the first rubber ring at a plurality of contacts provided at several positions and the diameter of said second rubber ring is larger than that of said first rubber ring.

5. The device according to claim 1, wherein said first and second attaching means comprise one or more pairs of magnets which face each other and have opposite polarities.

6. The device according to claim 1, further comprising a drain member provided at a position above the drain through hole of said filtered water storage unit, wherein said drain member is provided with a hole at its bottom and with a number of holes at its sidewall.

7. The device according to claim 1, further comprising a hollow extension part which downwardly extends from a lower edge of said filtered water storage unit, with a tube hole being formed at a predetermined position of a sidewall of said hollow extension part so that the drain tube passes through said tube hole.

8. The device according to claim 1, wherein said drain tube comprises a coiled portion at a position adjacent to the tube connecting the first through hole of said drain tank.

* * * * *